April 2, 1974 L. H. SHOESMITH Plant Pat. 3,536
CHRYSANTHEMUM PLANT (ST. MORITZ)
Filed Aug. 10, 1972
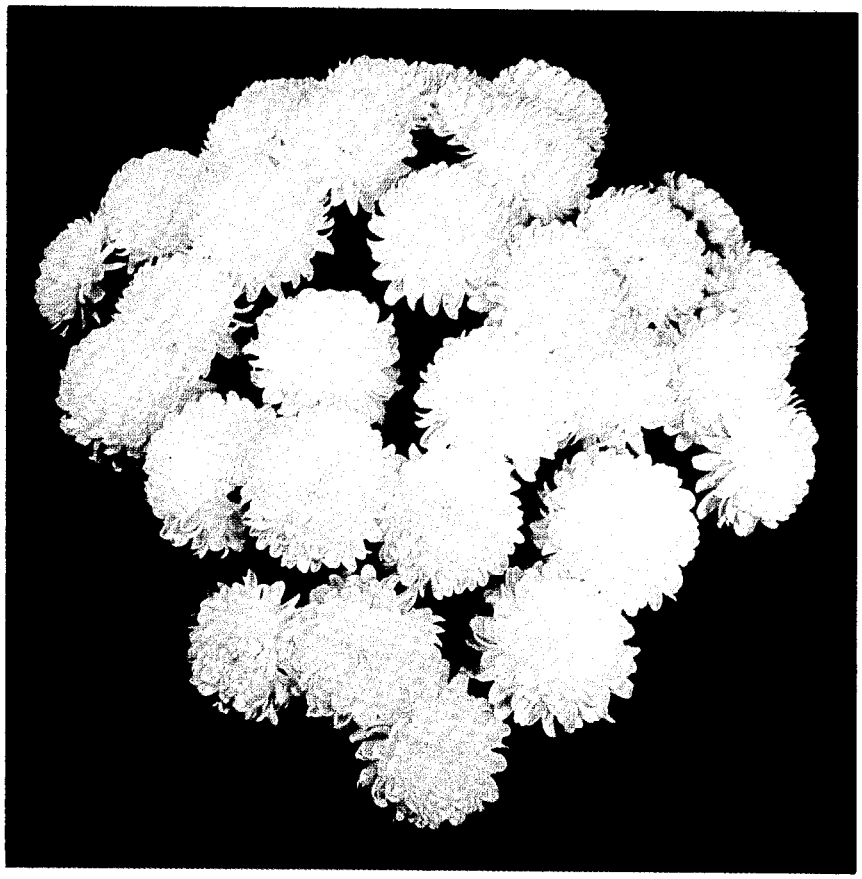
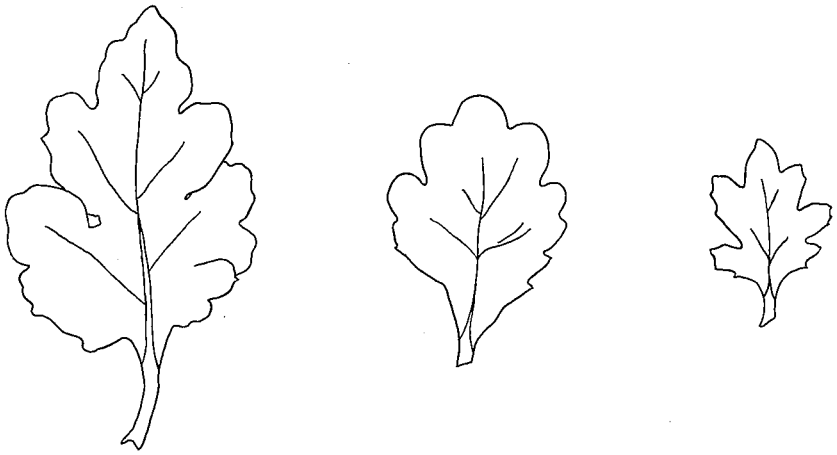

United States Patent Office

Plant Pat. 3,536

Patented Apr. 2, 1974

3,536

CHRYSANTHEMUM PLANT

Leonard H. Shoesmith, Westfield-Woking, England, assignor to Pan-American Plant Company, Chicago, Ill.

Filed Aug. 10, 1972, Ser. No. 279,513

Int. Cl. A01h 5/00

U.S. Cl. Plt.—77 1 Claim

ABSTRACT OF THE DISCLOSURE

A new variety of *Chrysanthemum morifolium* for greenhouse culture as a pot plant, distinguished by its relatively large pure white flower of semi-incurved form which can be brought to bloom the year around with photoperiod control, the new plant having a dependable nine-week response.

BACKGROUND OF THE NEW PLANT

This new variety of white chrysanthemum originated as a seedling of unknown parentage growing among a stock of greenhouse plants maintained under my direction at West Chicago, Ill., for use by me in the course of an extensive breeding program carried on with the object of producing new and improved varieties of chrysanthemum for the commercial market. This plant was discovered by me in November 1968 and was selected for propagation and trial because of its sturdy and vigorous growth and its production of very lovely pure white flowers of relatively large semi-globular form. Asexual propagation of this new plant under my direction at West Chicago, Ill., by means of cuttings, and subsequent trial has proved this varety to be capable of year around flowering, under photoperiod control, with a uniform nine-week response. Continued propagation of this new plant, by vegetative cuttings, at West Chicago, Ill., and at Cortez, Fla., has demonstrated that the distinctive characteristics of the original plant are firmly fixed and hold true for all succeeding asexually propagated generations of this new chrysanthemum variety.

DESCRIPTION OF THE DRAWING

My new chrysanthemum variety is illustrated by the accompanying drawing which shows the form and color characteristics of the flowers by means of conventional photographic procedures and which shows the configuration of typical leaves of this variety, by means of pen-and-ink drawings.

DESCRIPTION OF THE NEW PLANT

The following is a detailed description of this new variety of chrysanthemum plant with color designations according to the Horticultural Colour Chart by Robert F. Wilson, issued by the British Colour Council in collaboration with the Royal Horticultural Society of London, England.

*The plant*

Origin: Seedling.

Parentage: Unknown, this seedling having been selected from among many resulting from random crosses.

Classification:

*Botanic.*—Chrysanthemum morifolium.

*Commercial.*—Greenhouse pot plant.

Form: Perennial herbaceous bush.

Height: About 10 inches.

Growth: Terminal. Vigorous and upright with good characteristics of sturdiness and strength.

Branching: Much branching when terminal bud is removed.

Foliage: Abundant, producing as many as 11 leaves on 6 inches of stem.

*Leaf Size.*—4½ to 5 inches long by 2½ to 3 inches wide for the mature leaf.

*Shape.*—Ovate to obovate, lobed and very slightly serrated.

*Surface aspect.*—Glaucescent.

*Color.*—Upper side—Spinach Green 0960. Under side—Spinach Green 0960/3.

*Venation.*—Leaves are pinnately veined.

*Petioles.*—Absent, leaf is sessile.

*The bud*

Form: Globular.

Size: ½ inch in diameter when phyllaries are just breaking open.

Opening rate: Slow.

Color:

*When phyllaries first divide.*—Chartreuse Green 663/2.

*When florets begin to unfurl.*—Chartreuse Green 663/3.

Phyllaries: The outside of the receptacle bears many distinct involucral upstanding bracts.

*Color.*—Inside—Scheeles Green 860/1. Outside—Scheeles Green 860.

*Surface aspect.*—Canescent.

Calyx: The calyx is represented by tiny bristles arising from the top of the ovary, and occasionally may be absent.

Peduncle: ¾ inch to 1 inch long, erect with small modified leaf attached.

*Surface aspect.*—Canescent.

*The flower*

Response: Dependable 9 week.

Recommended flowering: Can be flowered the year around with photoperiod control.

Natural flowering season: Late October.

Blooms: Flower type—semi-incurved.

*Borne.*—A head of many florets borne on a receptacle.

*Size.*—Medium, 3½ to 4 inches in diameter; 2 to 2½ inches in depth.

*Shape.*—Flat when bloom first opens, becoming more globular as flower matures.

*Florets.*—Numerous ray florets. Form: Linear with obtuse apex, 2 to 2½ inches long. Color: Outer floret—White with Pod Green 061 base. Inside floret—White. Reverse side of florets—White.

*Firmness.*—Medium.

*Appearance.*—Satiny.

*Discoloration.*—None.

Peduncle: Sturdy and upright, ¾ inch to 1 inch long.

*Color.*—Scheeles Green 860.

Persistence: Florets hang on and dry.

Effect of weather and season change: None.

Lasting quality: The blooms are long lasting on plant and are not used as a cut flower.

*Reproductive organs*

Stamens: This plant does not seem to possess stamens and there is no pollen.

Pistils: Number—one for each ray floret.

*Style.*—About ¼ inch long.

*Stigmas.*—Color—Straw Yellow 604.

This new variety of chrysanthemum is intended for production as a greenhouse pot plant and is not used for cut flowers. This variety produces a well formed, strong stemmed plant having excellent and abundant dark green foliage which contrasts beautifully with its pure white, long enduring flowers; and for greenhouse culture this variety has a dependable nine-week response capable of producing flowering plants the year around.

I claim:

1. A new variety of crysanthemum plant, substantially as shown and described, characterized by its production of large white flowers of semi-incurved form on a very sturdy, strong stemmed, vigorous plant; by its abundant dark green foliage which provides excellent contrast for the white flowers; and by its ability to flower evenly and uniformly with a nine-week response.

No references cited.

ROBERT E. BAGWILL, Primary Examiner